United States Patent [19]

Moilliet

[11] 4,080,389
[45] Mar. 21, 1978

[54] ANAESTHETIC COMPOSITION

[75] Inventor: John Stewart Moilliet, Runcorn, England

[73] Assignee: Imperial Chemical Industries Limited, London, United Kingdom

[21] Appl. No.: 637,680

[22] Filed: Dec. 4, 1975

[30] Foreign Application Priority Data

Dec. 6, 1974 United Kingdom ............... 52834/74

[51] Int. Cl.$^2$ ....................... C07C 43/02; C07C 43/12
[52] U.S. Cl. ................................ 260/614 F; 424/342
[58] Field of Search ..................................... 260/614 F

[56] References Cited

U.S. PATENT DOCUMENTS 3,469,011  9/1969  Terrell .......................... 260/614 F X

OTHER PUBLICATIONS

Terrell et al., J. Of Med. Chem. (1971) vol. No. 6 517–519.

Primary Examiner—Howard T. Mars
Attorney, Agent, or Firm—Cushman, Darby & Cushman

[57] ABSTRACT

The compound 2-chloro-1,2,2-trifluoroethyl difluoromethyl ether, processes for its manufacture, compositions containing it and its use as an inhalation anaesthetic.

1 Claim, No Drawings

ANAESTHETIC COMPOSITION

This invention relates to a novel halogenated ether which possesses anaesthetic activity and which is substantially free from undesirable side-effects when administered to warm-blooded animals by inhalation.

According to the present invention there is provided the novel compound 2-chloro-1,2,2-trifluoroethyl difluoromethyl ether having the formula $CHF_2OCHFCClF_2$.

The structure of the compound is confirmed by the following physical data:

| Mass spectrum: principal ions | | |
|---|---|---|
| m/e | % intensity | ion |
| 149 | 2 | $CHF_2OCHFCF_2$ |
| 117/119 | 13/4 | $C_2F_3HCl$ |
| 101 | 10 | $C_2F_4O$ |
| 99 | 10 | $C_2F_3H_2O$ |
| 85/87 | 4/1 | $CF_2Cl$ |
| 71 | 8 | $CF_2H$ |
| 67/69 | 13/4 | $CHClF$ |
| 51 | 100 | $CHF_2$ |
| 29 | 78 | $CHO$ |

| Proton magnetic resonance spectrum (in carbon tetrachloride using tetramethylsilane as internal reference) | | |
|---|---|---|
| $\delta$ | | |
| 5.83 | doublet of triplets | —CHF— |
| 6.4 | triplet | —CHF$_2$ |

| $F^{19}$ magnetic resonance spectrum (in $CFCl_3$) | |
|---|---|
| 140.7 ppm doublet of multiplets | —CHF— |
| 86.2 ppm doublet AB system | —CHF$_2$ |
| 72.0 ppm doublet of doublets | —CF$_2$Cl |

The compound has a boiling point of 56° C. at normal atmospheric pressure.

According to a further feature of the invention there is provided a process for the manufacture of 2-chloro-1,2,2-trifluoroethyl difluoromethyl ether which comprises either the chlorination of difluoromethyl 1,2,2-trifluoroethyl ether ($CHF_2OCHFCHF_2$) or the fluorination of methyl 2,2,2-trichloroethyl ether ($CH_3OCH_2CCl_3$).

The chlorination process may conveniently be carried out at laboratory temperature using gaseous chlorine under the influence of ultraviolet radiation. The fluorination process may conveniently be carried out using a high-valency metal fluorinating agent, for example cobaltic fluoride, at an elevated temperature, for example at 60° C.

The $CHF_2OCHFCHF_2$ used as starting material is a known compound (Tetrahedron, 1971, 27, 4533 to 4551). The $CH_3OCH_2CCl_3$ used as starting material is a known compound (Bulletin de la Societe Chimique de France 1967, 1520–1532).

According to a further feature of the invention there is provided an inhalation anaesthetic composition which comprises as anaesthetic agent 2-chloro-1,2,2-trifluoroethyl difluoromethyl ether together with oxygen and optionally together with one or more other physiologically-acceptable material(s), the proportion of anaesthetic agent in the composition being such that when the composition is administered by inhalation to a warm-blooded animal anaesthesia is produced and/or maintained, and the proportion of oxygen in the composition being such that when the composition is administered by inhalation to a warm-blooded animal respiration is maintained.

It is to be understood that the 2-chloro-1,2,2-trifluoroethyl difluoromethyl ether must be free of toxic impurities when it is used in the composition of the invention.

The oxygen present in the composition of the invention may be pure oxygen, or it may be in the form of air, that is in a mixture with nitrogen and smaller quantities of other gases.

The other physiologically-acceptable material(s) that may optionally be present in the composition of the invention may be, for example, one or more substances selected from other inhalant anaesthetics, for example halothane, nitrous oxide, diethyl ether, divinyl ether, trifluoroethyl vinyl ether, cyclopropane, trichloroethylene, chloroform, enflurane, fluroxene, methoxyflurane, teflurane and 1-chloro-2,2,2-trifluoroethyl difluoromethyl ether; pharmaceutically-inert gases, for example nitrogen, chemically inert gases such as are present in air, for example neon and argon, and carbon dioxide and water vapour; and pharmaceutically-acceptable stabilisers which may be present to protect one or more of the other components of the composition from the effect of light, oxidation and/or attack by acid or base. As a suitable stabiliser there may be used, for example, a volatile stabilising agent which is physiologically tolerable, for example ethanol, or a non-volatile stabilising agent which is not carried over substantially during vaporisation, for example thymol.

The composition of the invention will usually contain between 0.25% and 3.5% volume by volume of the 2-chloro-1,2,2-trifluoroethyl difluoromethyl ether.

The composition of the invention may be administered to warm-blooded animals, including man, for the production of anaesthesia by conventional techniques. The composition may be performed and administered as such, or alternatively the 2-chloro-1,2,2-trifluoroethyl difluoromethyl ether and oxygen, either of which may have other physiologically-acceptable materials present with it, may be administered separately, the composition of the invention being formed either immediately prior to, or during, the course of administration. For example, the composition may be used in apparatus or machines adapted for the vaporisation of liquid anaesthetics and the admixture thereof with oxygen or with air or other gaseous mixtures containing oxygen in amount capable of supporting respiration.

According to a further feature of the invention there is provided an inhalation anaesthetic apparatus charged with 2-chloro-1,2,2-trifluoroethyl difluoromethyl ether.

According to a further feature of the invention there is provided a method for producing anaesthesia in a warm-blooded animal which comprises administering to said animal an anaesthetically-effective amount of 2-chloro-1,2,2-trifluoroethyl difluoromethyl ether together with sufficient oxygen to maintain respiration.

The invention is illustrated but not limited by the following Examples:

EXAMPLE 1

Chlorine gas was bubbled during 4 hours at a rate of 40 ml./minute through 40 ml. (57 g.) of difluoromethyl 1,2,2-trifluoroethyl ether ($CHF_2OCHFCHF_2$) under ultraviolet irradiation. Unreacted chlorine passed from the reaction vessel through a vertical air condenser and a dephleg, maintained at −78° C. with trichloroethylene/solid carbon dioxide, which condensed any organic components of the exit gases. The reaction mixture was then distilled into a cold trap, dried over a molecular sieve and finally separated into its components on a preparative gas-liquid chromatogram using a 30 ft. column containing 20% by weight of diethyl hexyl sebacate supported on 'Celite' (Registered Trade Mark).

2-Chloro-1,2,2-trifluoroethyl difluoromethyl ether was obtained in about 6% yield based on difluoromethyl 1,2,2-trifluoroethyl ether.

EXAMPLE 2

Methyl 2,2,2-trichloroethyl ether (56 ml.) was added during 5 hours to a reactor containing cobalt (III) fluoride (2000 g.) which was stirred and maintained at 60° C. Nitrogen was then blown through the stirred reactor contents for 1 hour, the material entrained by the nitrogen being condensed and collected in a trap maintained at −75° C. The contents of the trap were washed with water and dried over molecular sieve, 45 g. of material being produced.

The combined product from ten such reactions was fractionally distilled and the desired fraction further purified by gas chromatography using a 30 ft. × 0.5 inch column containing 20% by weight of a polyethylene glycol ('Carbowax' M; Registered Trade Mark) supported on 'Celite'. There was thus obtained 2-chloro-1,2,2-trifluoroethyl difluoromethyl ether (120 g.).

EXAMPLE 3

A group of 6 mice is placed in a chamber of 10 liters capacity which contains solid soda lime, and a mixture of 2-chloro-1,2,2-trifluoroethyl difluoromethyl ether and oxygen, of known percentage, is released into the chamber. A reservoir bag containing the known percentage mixture is used to maintain atmospheric pressure as the mixture is inhaled by the mice and as exhaled carbon dioxide is absorbed by the soda lime. After 30 minutes the concentration of 2-chloro-1,2,2-trifluoroethyl difluoromethyl ether in the chamber is determined by gas chromatography.

The experiment is repeated using different mixtures of 2-chloro-1,2,2-trifluoroethyl difluoromethyl ether and oxygen, and the $AC_{50}$, that is the concentration by volume of 2-chloro-1,2,2-trifluoroethyl difluoromethyl ether which anaesthetises 3 mice out of 6 after 30 minutes exposure, is found to be 0.9%. The $LC_{50}$, that is the concentration by volume of 2-chloro-1,2,2-trifluoroethyl difluoromethyl ether which kills 3 mice out of 6 after 30 minutes exposure, is found to be 4.2%. The therapeutic ratio of the compound is therefore 4.2/0.9, that is 4.7. Under similar conditions the $AC_{50}$, $LC_{50}$ and therapeutic ratio for halothane are respectively 0.85%, 3.4% and 4.0.

EXAMPLE 4

A mixture of 2-chloro-1,2,2-trifluoroethyl difluoromethyl ether (3% v/v) and air (97% v/v) was administered to a cat for a period of 10 minutes. Induction of anaesthesia and subsequent recovery from anaesthesia were smooth, and rapid.

EXAMPLE 5

A cat was anaesthetised by injection of a 2.5% w/v solution of thiopentone sodium in water into a cephalic vein at a dose equivalent to 20 mg./kg. bodyweight. Anaesthesia was subsequently maintained by administration of a mixture of 2-chloro-1,2,2-trifluoroethyl difluoromethyl ether (1% v/v) and oxygen (99% v/v) contained in a large nylon reservoir bag. Aanesthesia was maintained in this way for 40 minutes. Mean arterial pressure and heart rate during this period were both substantially higher than under comparable anaesthesia with halothane.

What we claim is:

1. The compound 2-chloro-1,2,2-trifluoroethyl difluoromethyl ether having the formula $CHF_2OCHFCClF_2$.

* * * * *